United States Patent
Wei et al.

(10) Patent No.: US 12,065,686 B2
(45) Date of Patent: Aug. 20, 2024

(54) METHOD FOR PRODUCING CITRIC ACID BY DEGRADING ROUGHAGES WITH THE RUMEN FUNGUS-METHANOGEN CO-CULTURE FROM QINGHAI YAKS

(71) Applicant: INSTITUTE OF BIOLOGY, GANSU ACADEMY OF SCIENCES, Tanzhou (CN)

(72) Inventors: Yaqin Wei, Ianzhou (CN); Zhiye Wang, Ianzhou (CN); Jiang Zhao, Ianzhou (CN)

( * ) Notice: Subject to any disclaimer, the term of this patent is extended or adjusted under 35 U.S.C. 154(b) by 0 days.

(21) Appl. No.: 17/789,228

(22) PCT Filed: Dec. 28, 2021

(86) PCT No.: PCT/CN2021/141840
§ 371 (c)(1),
(2) Date: Jun. 27, 2022

(87) PCT Pub. No.: WO2022/143581
PCT Pub. Date: Jul. 7, 2022

(65) Prior Publication Data
US 2024/0011060 A1    Jan. 11, 2024

(30) Foreign Application Priority Data
Dec. 30, 2020 (CN) .......................... 202011616690.5

(51) Int. Cl.
| | |
|---|---|
| *C12P 7/48* | (2006.01) |
| *C12N 1/14* | (2006.01) |
| *C12N 1/20* | (2006.01) |
| *C12P 39/00* | (2006.01) |
| *C12R 1/26* | (2006.01) |
| *C12R 1/645* | (2006.01) |

(52) U.S. Cl.
CPC ................ *C12P 7/48* (2013.01); *C12N 1/145* (2021.05); *C12N 1/205* (2021.05); *C12P 39/00* (2013.01); *C12R 2001/26* (2021.05); *C12R 2001/645* (2021.05)

(58) Field of Classification Search
CPC ........................... C12P 39/00; C12P 7/00–625
See application file for complete search history.

(56) References Cited

U.S. PATENT DOCUMENTS

| | | |
|---|---|---|
| 2002/0111508 A1 | 8/2002 | Bergrath et al. |
| 2012/0053303 A1 | 3/2012 | Djuric et al. |
| 2020/0231929 A1 | 7/2020 | Shi et al. |

FOREIGN PATENT DOCUMENTS

| | | |
|---|---|---|
| CN | 106978355 A | 7/2017 |
| CN | 112553284 | 3/2021 |
| WO | 2010124147 A | 10/2010 |

OTHER PUBLICATIONS

ISR of PCT/CN2021/141840.
Li, Yuanfei, "Investigation of the Effect of Methanogens on the Metabolism of Anaerobic Fungi by Co-culture Technique", Chinese Doctoral Dissertations Full-Text Database,Jul. 15, 2020 (Jul. 15, 2020).
Cheng YF et al. "Production of Citrate by Anaerobic Fungi in the Presence of Co-culture Methanogens as Revealed by 1H NMR Spectrometry", Asian-Australasian Journal of Animal Sciences, Oct. 31, 2013 (Oct. 31, 2013).
Li YQ et al."Co-cultured methanogen improved the metabolism in the hydrogenosome of anaerobic fungus as revealed by gas chromatography-mass spectrometry analysis", Asian-Australasian Journal of Animal Sciences,Jan. 13, 2020 (Jan. 13, 2020).
Li, Yuanfei et al. "Advance in the Co-culture of Anaerobic Fungi and Methanogens",Acta Microbiologica Sinica, Oct. 10, 2020 (Oct. 10, 2020).
CNIPA, Notification of First Office Action for Chinese application CN202011616690.5, Aug. 18, 2021.
CNIPA, Notification to grant patent right for Chinese application CN202011616690.5, Nov. 15, 2021.

*Primary Examiner* — Thane Underdahl
(74) *Attorney, Agent, or Firm* — Zhigang Ma

(57) ABSTRACT

The present disclosure relates to the technical field of biotechnology renewable energy, and more specifically, to a method for producing citric acid by degrading roughage with natural symbiotic mixed culture. The mixed culture YakQH5 is composed of anaerobic fungi (*Neocallimastix frontalis*) and methanogens (*Methanobrevibacter gottschalkii*). It was collected in the China General Microbiological Culture Collection Center on Mar. 9, 2020, with the collection number of CGMCC No. 19299. The mixed culture YakQH5 can degrade 15 kinds of roughage respectively and produce a large amount of citric acid. Especially when alfalfa is used as substrate, the yield of citric acid is as high as 46.0 mm. Adding compound antibiotics in the fermentation process can also prevent the mixed culture from being polluted by bacteria in the fermentation process and further improve the efficiency of anaerobic fermentation. The mixed culture YakQH5 has important industrial application value.

2 Claims, No Drawings

METHOD FOR PRODUCING CITRIC ACID BY DEGRADING ROUGHAGES WITH THE RUMEN FUNGUS-METHANOGEN CO-CULTURE FROM QINGHAI YAKS

CROSS REFERENCE TO RELATED APPLICATION

This patent application claims the benefit and priority of Chinese Patent Application No. 202011616690.5 filed on Dec. 30, 2020, the disclosure of which is incorporated by reference herein in its entirety as part of the present application.

TECHNICAL FIELD

The present disclosure relates to the technical field of biotechnology renewable energy, and more specifically, to a method for producing citric acid by degrading roughage with the natural fungus-methanogen co-culture.

BACKGROUND ART

Roughage refers to the feed with natural moisture content less than 60%, crude fiber content equal to or higher than 18% in dry matter and fed in the form of air-dried matter, such as forage grass, crop straw, leaves, distiller's grains and chaff husks. The main component of roughage is lignocellulose, with high fiber content, low protein and mineral content, poor palatability and low digestibility of livestock and poultry, which limits its application. The amount of these roughage produced every year is very huge, such as wheat straw, corn straw, rice straw, oat straw, soya straw, soybean straw, potato straw, alfalfa, bran, distiller's grains, tomato residue, wheat husk, etc., which have not been reasonably developed and utilized as energy materials. At present, biological methods are mainly used, that is, microorganisms that can secrete high-efficiency lignocellulose degrading enzymes are used to degrade and utilize a large amount of roughage. However, there is an extreme lack of microbial strain resources to effectively improve the utilization rate of lignocellulose in roughage and realize the biotransformation of lignocellulose. How to establish efficient biotransformation technology and realize the biotransformation of lignocellulose is the fundamental way to solve the huge roughage resources.

The yak (*Bos grunniens*) is an herbivorous ruminant that lives at the highest altitude, is resistant to rough feeding and cold, and can adapt to high cold and hypoxia. Qinghai-Tibetan Plateau is the main yak producing area. Yaks in China are mainly raised by grazing. Yak rumen is inhabited by a large number of unique, complex and diverse microbial communities, which cooperate to degrade low-quality wild forage grass and cold season dry grass, provide survival energy and nutrients for yak, and make yak rumen become a natural anaerobic fermentation tank for efficient degradation of lignocellulose. Them are co-cultures of naturally symbiotic anaerobic fungi and methanogens in yak rumen. They can secrete highly active lignocellulose degrading enzymes to degrade wild forage grass and dry forage grass, so as to provide nutrition for yak growth. Therefore, the isolation of natural fungus-methanogen co-culture from yak rumen to degrade cheap lignocellulosic substrates to produce metabolic end products such as acetic acid and methane is of great significance in industrial applications.

Citric acid (chemical name: 2-hydroxy-homopropyl tricarboxylic acid) is an important organic acid. It has colorless crystals and often contains a molecule of crystal water. It is widely used in chemical and textile industry, food industry, environmental protection industry, poultry and livestock industry, cosmetics industry, medicine and other industries. C. W. Scheler first prepared citric acid by adding lime milk to fruit fluid to form calcium citrate precipitation in 1784. In China, citric acid was produced by fermentation, which was first reported by TengHan Tang in 1942 In 1952, Sheng Chen and others began to produce citric acid by shallow tray fermentation with *Aspergillus niger*. In 1965, a pilot experiment was carried out to produce citric acid by shallow tray fermentation of 100 t beet molasses raw material, which was put into production in 1968. After 1966, Tianjin Institute of Industrial Microbiology and Shanghai Institute of Industrial Microbiology successively carried out experimental research on the production of citric acid by submerged fermentation of dried potato powder raw materials using *Aspergillus niger*, and achieved success. Therefore, the main process route of citric acid production in China was determined. Its process is simple, does not need to add nutrients and has high yield. It is a unique and advanced process in China. China's research on the production of citric acid by petroleum fermentation is earlier. In 1970, research units in Tianjin, Shanghai, Shenyang and other places used *Candida lipolytica* to ferment paraffin oil to produce citric acid. In 1979, Ziyuan Xu and others screened the mutant *Candida lipolytica* sensitive to fluoroacetic acid, which significantly improved the yield of citric acid in petroleum fermentation. At present, with the application of high-yield strains and the continuous development of new technologies, the yield of citric acid fermentation and extraction have been significantly improved, and the citric acid industry has developed by leaps and bounds.

The inventor first studied the anaerobic fermentation of the rumen fungus-methanogen co-culture from grazing yak in Qinghai Province, using wheat straw, corn straw and rice straw as substrates respectively for the first time during doctoral study (Yaqin Wei. Study on the diversity and fiber degradation characteristics of fungus-methanogen co-cultures in the yak rumen [D]. 2016). The effect of the fungus-methanogen co-cultures on straw degradation was evaluated by detecting gas production, polysaccharide hydrolase activity, various esterase activities, dry matter degradation rate, phenolic acid release, methane and acetic acid production. Among them, the fungus-methanogen co-cultures *N. frontalis* Yak16+*M. ruminantium*, *Piromyces* Yak18+*M. ruminantium* and *O. joyonii* Yak7+*M. ruminantium* degraded the three straws with high yields of acetic acid and methane, but very low yields of citric acid, so the data of citric acid was not listed in the doctoral thesis. So far, there are no reports around the world on the production of citric acid by anaerobic fungi, or fungus-methanogen co-cultures degrading roughages such as straw.

SUMMARY

In view of the above technical problems, an object of the present disclosure is to provide a method for producing citric acid by degrading roughage with natural anaerobic fungus-methanogen co-culture. The natural anaerobic fungus-methanogen co-culture is composed of anaerobic fungi (*Neocallimastix frontalis*) and methanogens (*Methanobrevibacter gottschalkii*), namely, the *N. frontalis*+*M. gottschalkii* co-culture YakQH5, short name YakQH5. and the method includes the following steps.

(1) Preparation of the *N. frontalis*+*M. gottschalkii* co-culture YakQH5 inoculum: the mixed culture YakQH5 is inoculated into an anaerobic medium with wheat straw as substrate at an inoculation amount of 10% v/v, the compound antibiotics is added, and anaerobic culture is performed to obtain the high-activity inoculum.

(2) Fermentation and degradation of roughages to produce citric acid: the inoculum prepared in step (1) is absorbed and inoculated into an anaerobic medium with 1% w/v roughage as substrate according to an inoculation amount of 10% v/v. 1% v/v compound antibiotics are added at the same time, and the culture is performed.

Preferably, the *N. frontalis*+*M. gottschalkii* co-culture YakQH5 having a collection number of CGMCC No 19299, has been preserved in China General Microbiological Culture Collection Center (CGMCC), Institute of Microbiology, Chinese Academy of Sciences, No. 1 West, Beichen Road, Chaoyang District Beijing China, on Mar. 9, 2020, and is named YakQH5 (the co-culture of *Neocallimastix frontalis* and *Methanobrevibacter gottschalkii*).

Preferably, in the step (1), the temperature of anaerobic culture is 39° C., and the time is 72 hours. In step (2), the temperature of anaerobic culture is 39° C., and the time is 5 days.

Preferably, the compound antibiotics are penicillin sodium and streptomycin sulfate, and the concentrations in the anaerobic medium are 1600 IU/mL and 2000 IU/mL, respectively.

Preferably, the formula of the anaerobic medium is as follows: yeast extract 1.0 g, peptone 1.0 g, $NaHCO_3$ 7.0 g, resazurin (1.0 g/l) 1 mL, L-cysteine hydrochloride 1.7 g, rumen fluid collected before morning feeding 8000×g, 170 mL of supernatant after centrifugation at 4° C. for 20 min, salt solution I 82.5 mL, salt solution II 16.5 mL, and distilled water to make up to 1000 mL.

Preferably, the formula of the salt solution I is as follows: NaCl 6 g, $(NH_4)_2SO_4$ 3 g, $KH_2PO_4$ 3 g, $CaCl_2 \cdot 2H_2O$ 0.4 g, $MgSO_4 \cdot 2H_2O$ 0.6 g, and distilled water to make up to 1000 mL.

Preferably, the formula of the salt solution II is as follows: $K_2HPO_4$ 4 g, and distilled water to make up to 1000 mL.

Preferably, the step (2) includes deoxygenating after adding various substrates respectively, filling carbon dioxide, and sterilizing at high temperature and high pressure.

Preferably, the substrates added in step (2) are one or more of wheat straw, flax straw, potato straw, cotton straw, soybean straw, sainfoin straw, reed straw, sisal, bran, melon seed husk, peanut husk, wheat husk, filter paper, tomato residue and alfalfa.

Preferably, the substrate added in step (2) is alfalfa.

The beneficial effects of the disclosure are as follows. ①. the natural co-culture YakQH5 of anaerobic fungi (*Neocallimastix frontalis*) and methanogens (*Methanobrevibacter gottschalkii*) in the present disclosure is isolated from yak rumen fluid. Microorganisms in yak rumen cooperate to degrade low-quality weeds, provide yak with nutrients necessary for survival, and enable yak to adapt to the harsh environment of the Qinghai-Tibetan Plateau. Due to long-term natural selection and evolution, yak rumen has become a highly efficient lignocellulose degrading enzyme system. Compared with the artificial mixed fungus-methanogen co-cultures, the naturally existing fungus-methanogen co-cultures in yak rumen has significant advantages in highly degrading lignocellulose. ②. The *N. frontalis*+*M. gottschalkii* co-culture YakQH5 was used for anaerobic fermentation to degrade 15 kinds of roughage, including wheat straw, flax straw, potato straw, cotton straw, soybean straw, sainfoin straw, reed straw, sisal, bran, melon seed husk, peanut husk, wheat husk, filter paper, tomato residue and alfalfa. The citric acid concentration produced by degrading alfalfa (i.e. alfalfa as substrate) was 46.0 mM, which was significantly higher than that of other substrates. ③. Adding compound antibiotics in the fermentation process can prevent the co-culture system from being polluted by bacteria and improve the efficiency of anaerobic fermentation. ④. At the same time, the co-culture used in the disclosure can survive and pass in vitro through collection, which is convenient for popularization and provides great convenience for production.

DETAILED DESCRIPTION OF THE EMBODIMENTS

The experimental methods used in the following embodiments are conventional methods unless otherwise specified.

The materials, reagents, etc. used in the following embodiments can be obtained from commercial sources unless otherwise specified.

The culture media used in the following examples are as follows.

The formula of the anaerobic medium was as follows: yeast extract 1.0 g, peptone 1.0 g, $NaHCO_3$ 7.0 g, resazurin (1.0 g/l) 1 mL, L-cysteine hydrochloride 1.7 g, rumen fluid collected before morning feeding 8000×g, 170 mL of supernatant after centrifugation at 4° C. for 20 min, salt solution I 165 mL, salt solution II 165 mL, and distilled water to make up to 1000 mL.

The formula of the salt solution I was as follows: NaCl 6 g, $(NH_4)_2SO_4$ 3 g, $KH_2PO_4$ 3 g, $CaCl_2 \cdot 2H_2O$ 0.4 g, $MgSO_4 \cdot 2H_2O$ 0.6 g, and distilled water to make up to 1000 mL.

The formula of the salt solution II was as follows: $K_2HPO_4$ 4 g, and distilled water to make up to 1000 mL.

Subculture medium: 1% w/v crushed and air-dried wheat straw was added to the anaerobic medium. Then the sterilization was performed after deaeration.

Deaeration method: the anaerobic pipe or anaerobic bottle was connected to the air extraction device with vacuum pump and high-purity $CO_2$ through the needle to deaerate the culture medium. Firstly, when the gas in the vacuum pump extraction pipe reached negative pressure, the color of the culture medium changed, and then the high-purity $CO_2$ was filled. Each pipe was pumped and inflated for 3 times, of which the first time was about 15 min, and the other two times were 5 min each time. After the last inflation, the sterile needle was used to deflate again to balance the internal and external pressure of the anaerobic pipe, and the sterilization was performed at 121° C. high temperature, high pressure and damp heat for 20 minutes for standby.

Anaerobic fermentation tank, also known as anaerobic fermentation bottle, is a closed tank, in which the process of material liquid fermentation and biogas production is completed. It is mainly used to meet the living conditions of microorganisms and make them live in a suitable environment, so as to achieve the purpose of vigorous fermentation and high gas production.

Embodiment 1: Preparation of the *N. frontalis*+*M. Gottschalkii* Co-Culture YakQH5

1 mL the *N. frontalis*+*M. gottschalkii* co-culture YakQH5 was taken and inoculated into 9 ml of anaerobic medium with air dried and crushed wheat straw as substrate in Heinz anaerobic pipe. At the same time, 0.1 mL of compound antibiotics (1600 IU/mL penicillin and 2000 IU/ml streptomycin sulfate) were added. Anaerobic culture was performed at 39° C. for 72 h to reach the growth peak. At this time, the fermentation broth was a highly active inoculum.

Embodiment 2: Fermentation of the N. frontalis+M. Gottschalkii Co-Culture YakQH5 to Produce Citric Acid 45 mL liquid basic medium was filled in a 100 mL volume anaerobic fermentation bottle. A total of 15 kinds of roughage, including 0.5 g crushed air-dried wheat straw, flax straw, potato straw, cotton straw, soybean straw, sainfoin straw, reed straw, sisal, bran, melon seed husk, peanut husk, wheat husk, filter paper, tomato residue and alfalfa, was used as substrates respectively. Then the deaeration and sterilization were performed. The mixed culture YakQH5 subcultured for 72 h was inoculated into the above-mentioned anaerobic medium with each roughage by drawing 5 mL with a sterile syringe. At the same time, 0.5 mL of compound antibiotics (1600 IU/mL penicillin and 2000 IU/mL streptomycin sulfate) were added. Anaerobic culture was performed at 39° C. for 5 days. Three parallel experiments were set up to measure the citric acid concentration in the anaerobic bottle every 24 hours. Citric acid was determined by liquid chromatography.

The liquid chromatograph (LC2030 PLUS, Shimadzu, Japan) was used and equipped with Acclaim 120 C18 3 um column (21 mm×50 mm). The detection wavelength was 210 nm, column temperature was 25° C., UV detector temperature was 40° C., and mobile phase A: potassium phosphate aqueous solution (pH 2), mobile phase B: acetonitrile, flow rate 0.5 m/min, 0 min 99% A-1% CB, 20 m 80% A-20% B, injection volume 10 µL. The experimental results showed that the N. frontalis+M. gottschalkii co-culture YakQH5 degraded 15 kinds of roughages and produced high concentration citric acid. The yield of citric acid produced with alfalfa as substrate was significantly higher than that of other substrates. The specific results are as follows.

TABLE 1

Yield of citric acid produced by degradation of 15 kinds of roughages with the N. frontalis + M. gottschalkii co-culture YakQH5 from Qinghai yaks.

| | | Citric acid concentration (mM) | | | | |
|---|---|---|---|---|---|---|
| No. | Roughage substrate | 2d | 3d | 4d | 5d | Average |
| 1 | Wheat straw | 5.0$^c$ | 11.7$^b$ | 23.6$^c$ | 32.8$^d$ | 18.3$^b$ |
| 2 | Flax straw | 3.9$^b$ | 10.9$^b$ | 21.5$^c$ | 28.2$^c$ | 16.1$^b$ |
| 3 | Potato straw | 3.0$^b$ | 12.5$^b$ | 26.1$^c$ | 31.0$^c$ | 18.2$^b$ |
| 4 | Cotton straw | 1.0$^a$ | 8.2$^b$ | 15.9$^b$ | 20.0$^c$ | 11.3$^b$ |
| 5 | Soybean straw | 3.8$^b$ | 9.5$^b$ | 16.4$^b$ | 27.1$^c$ | 14.2$^b$ |
| 6 | Sainfoin straw | 9.1$^d$ | 20.3$^d$ | 38.6$^d$ | 40.1$^d$ | 27.0$^c$ |
| 7 | Reed straw | 2.0$^b$ | 14.1$^c$ | 20.5$^c$ | 24.6$^c$ | 15.3$^b$ |
| 8 | Sisal | 3.5$^b$ | 13.8$^b$ | 22.0$^c$ | 27.8$^c$ | 16.8$^b$ |
| 9 | Bran | 2.0$^b$ | 7.6$^a$ | 10.5$^a$ | 16.3$^b$ | 9.1$^a$ |
| 10 | Melon seed husk | — | — | — | — | — |
| 11 | Peanut husk | — | — | — | — | — |
| 12 | Wheat husk | 4.6$^c$ | 12.0$^c$ | 18.7$^b$ | 20.7$^c$ | 14.0$^b$ |
| 13 | Filter paper | 3.2$^b$ | 10.2$^b$ | 17.0$^b$ | 21.4$^c$ | 12.9$^b$ |
| 14 | Tomato residue | 1.0$^a$ | 5.1$^a$ | 9.3$^a$ | 11.5$^a$ | 6.7$^a$ |
| 15 | Alfalfa | 12.3$^d$ | 26.5$^d$ | 37.9$^d$ | 46.0$^d$ | 30.7$^d$ |

Note:
—, means not measured.
$^a$, $^b$, $^c$ and $^d$ indicate statistical difference (p < 0.05).

The experimental results are shown in Table 1. The N. frontalis+M. gottschalkii co-culture YakQH5 degraded 15 kinds of roughage respectively during the 5-day culture period to produce citric acid, and the highest yields are as follows. The yield of citric acid produced by fermentation with wheat straw as substrate reached 32.8 mM, the yield of citric acid produced by fermentation with flax straw as substrate reached 28.2 mM, the yield of citric acid produced by fermentation with potato straw as substrate reached 31.0 mM, the yield of citric acid produced by fermentation with cotton straw as substrate reached 20.0 mM, the yield of citric acid produced by fermentation with soybean straw as substrate reached 27.1 mM, the yield of citric acid produced by fermentation with sainfoin straw as substrate reached 40.1 mM, the yield of citric acid produced by fermentation with reed straw as substrate reached 24.6 mM, the yield of citric acid produced by fermentation with sisal as substrate reached 27.8 mM, the yield of citric acid produced by fermentation with bran as substrate reached 16.3 mM, the yield of citric acid produced by fermentation with wheat husk as substrate reached 20.7 mM, the yield of citric acid produced by fermentation with filter paper as substrate reached 21.4 mM, the yield of citric acid produced by fermentation with tomato residue as substrate reached 11.5 mM, and the yield of citric acid produced by fermentation with alfalfa as substrate reached 46.0 mM.

It can be seen from the above embodiments that the natural fungus—methanogen co-cultures—the N. frontalis+ M. gottschalkii co-culture YakQH5 from the rumen of Qinghai yaks can degrade 15 kinds of roughage and produce a large amount of citric acid at the same time. In particular, the citric acid produced by degraded alfalfa reaches the highest value of 46.0 mm, which has important industrial application value.

What is claimed is:
1. A method for producing citric acid by degrading roughage with YakOH5, wherein YakOH5 is a natural co-culture isolated from the rumen of Qinghai yaks that comprises N. frontalis and M. gottschalkii, and the method comprises the following steps:
S1) Preparation of the YakQH5 inoculum by: inoculating the YakQH5 into an anaerobic medium with wheat straw as substrate at an inoculation amount of 10% v/v, adding antibiotics and performing anaerobic culture to obtain high-activity inoculum; and
S2) Fermentation and degradation of roughage to produce citric acid in a vessel by: collecting the inoculum prepared in step S1, inoculating it into an anaerobic medium with 1% w/v roughage as substrate according to an inoculation amount of 10% v/v, adding 1% v/v compound antibiotics at the same time, fermenting this inoculated anaerobic medium to degrade the roughage until citric acid is produced, and isolating the citric acid;
in the step S1, the temperature of anaerobic culture is 39° C. for 72 hours;
in step S2, the temperature of anaerobic culture is 39° C., for 5 days;
the antibiotics are penicillin sodium and streptomycin sulfate, and the concentrations in the anaerobic medium are 1600 IU/mL and 2000 IU/mL respectively;
the formula of the anaerobic medium is as follows:
1.0 g yeast extract,
1.0 g peptone,
7.0 g NaHCO$_3$,
1 ml of 1.0 g/L reazurin,
1.7 g L-cysteine hydrochloride,
170 mL of rumen fluid supernatant obtained by centrifuging rumen fluid collected from the Qinghai yaks before morning feeding at 8000×g centrifugation at 4° C. for 20 min, then isolating the supernatant,
82.5 mL salt solution I,
16.5 mL salt solution II, and
1000 ml distilled water;
wherein the formula of the salt solution I is as follows:
6 g NaCl;
3 g $(NH_4)_2SO_4$,
3 g $KH_2PO_4$,
0.4 g $CaCl_2 \cdot 2H_2O$,
0.6 g $MgSO_4 \cdot 2H_2O$, and
distilled water to make up to 1000 mL; and
wherein the formula of the salt solution II is as follows:
4 g $K_2HPO_4$,
And distilled water to make up to 1000 ml;
S2 comprises deoxygenating the vessel after adding the substrates by filling it with carbon dioxide, and sterilizing it at high temperatures and high pressure;
the substrates added in step S2 are selected from the group consisting of wheat straw, flax straw, potato straw, cotton straw, soybean straw, sainfoin straw, reed straw, sisal, bran, wheat husk, filter paper, tomato residue, and alfalfa.

2. The method of claim 1, wherein the substrate added in step S2 is alfalfa.

* * * * *